(12) United States Patent
Hasenbank et al.

(10) Patent No.: US 7,659,089 B2
(45) Date of Patent: Feb. 9, 2010

(54) CHEMICAL SENSOR ENHANCED BY DIRECT COUPLING OF REDOX ENZYME TO CONDUCTIVE SURFACE

(75) Inventors: Melissa S. Hasenbank, Seattle, WA (US); Elain S. Fu, Seattle, WA (US); Paul Yager, Seattle, WA (US)

(73) Assignee: University of Washington, Seattle, WA (US)

( * ) Notice: Subject to any disclaimer, the term of this patent is extended or adjusted under 35 U.S.C. 154(b) by 210 days.

(21) Appl. No.: 12/045,999

(22) Filed: Mar. 11, 2008

(65) Prior Publication Data

US 2008/0153121 A1    Jun. 26, 2008

Related U.S. Application Data

(62) Division of application No. 11/364,436, filed on Feb. 28, 2006, now Pat. No. 7,364,886.

(51) Int. Cl.
*C12N 11/00*    (2006.01)
*C12Q 1/26*    (2006.01)

(52) U.S. Cl. .......................................... 435/25; 435/174
(58) Field of Classification Search ........................ None
See application file for complete search history.

(56) References Cited

U.S. PATENT DOCUMENTS

| | | | |
|---|---|---|---|
| 4,224,125 | A | 9/1980 | Nakamura et al. |
| 5,089,112 | A | 2/1992 | Skotheim et al. |
| 6,218,134 | B1 | 4/2001 | Yamauchi et al. |
| 6,649,361 | B1 | 11/2003 | Iwasaki et al. |

OTHER PUBLICATIONS

Gorton, L., et al., "Direct electron transfer between heme-containing enzymes and electrodes as basis for third generation biosensors", Analytica Chimica ACTA, 1999 400:91-108.

Habermuller, L., "Electron-transfer mechanisms in amperometric biosensors", Fresenius Journal of Analytical Chemistry, 2000, 366(6-7):560-568.

Iwasaki, Y., "Imaging of electrochemical enzyme sensor on gold electrode using surface plasmon resonance", Biosens Bioelectron, Sep. 2002, 17(9):783-8 (1-Page Abstract Only).

Patolsky, F., "Precipitation of an insoluble product on enzyme . . . analyses", Anal. Chem., 1999, 71, 3171-3180.

Pyo, H.B. et al., "Multichannel surface plasmon resonance imaging and analysis of micropatterned . . . interactions", Langmuir, 2005, 21(1):166-171.

*Primary Examiner*—Rebecca E. Prouty
*Assistant Examiner*—Paul C. Martin
(74) *Attorney, Agent, or Firm*—Karen S. Canady; canady + lortz LLP

(57) ABSTRACT

The invention provides a method, apparatus and system for detecting electrochemical oxidoreduction activity mediated by a redox enzyme at a site remote from the enzyme. In one embodiment, the method comprises immobilizing the redox enzyme on a first region of a conductive surface and contacting a substrate capable of producing a detectable signal upon oxidation or reduction with a second region of the conductive surface. The second region is electrically coupled with the first region and the redox enzyme is not present in the second region. The method further comprises exposing the immobilized redox enzyme to conditions that effect oxidation or reduction of the enzyme, and detecting oxidation or reduction of the substrate at the second region. The invention can be adapted for detecting a plurality of analytes.

15 Claims, 8 Drawing Sheets

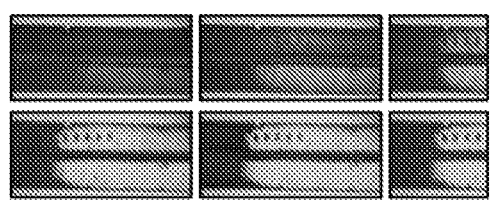
FIG. 5
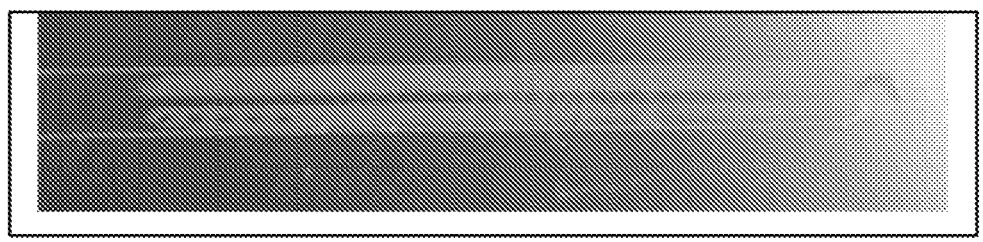
FIG. 6
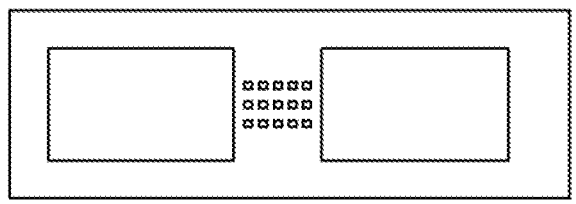
FIG. 7
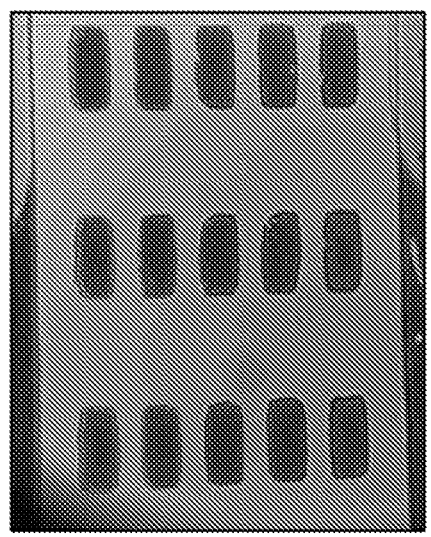 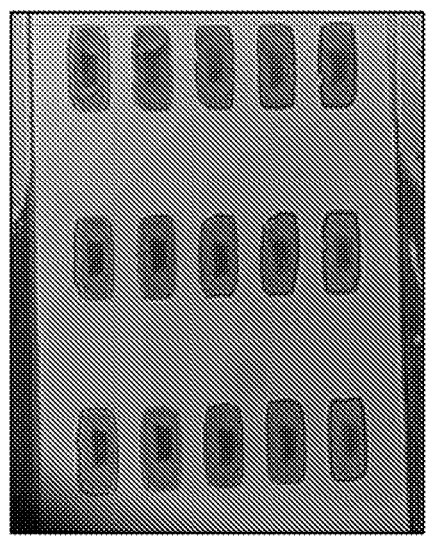
FIG. 8   FIG. 9

1. Pattern HRP on zone A of a bare gold film

2. Fill zone B with plain BSA

3. Add H$_2$O$_2$, which rapidly diffuses to HRP layer and oxidizes HRP.

- Hydrogen peroxide
- TMB
- Blue oxidized TMB

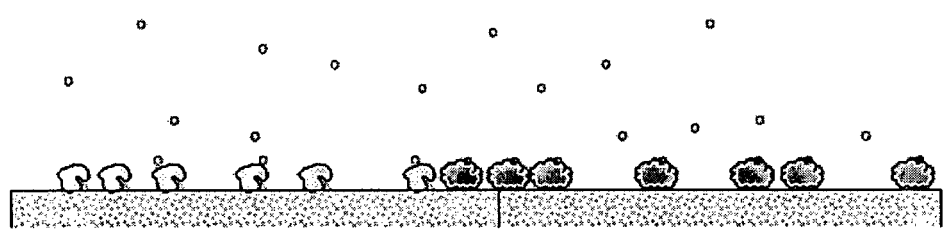

4. Add TMB to whole system

- Hydrogen peroxide
- TMB
- Blue oxidized TMB

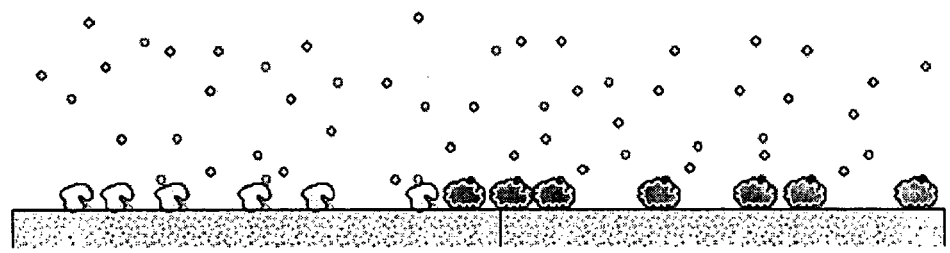

5. Electrons move from zone B to zone A; TMB converts to blue precipitate primarily at bare gold between BSA in zone B

- Hydrogen peroxide
- TMB
- Blue oxidized TMB

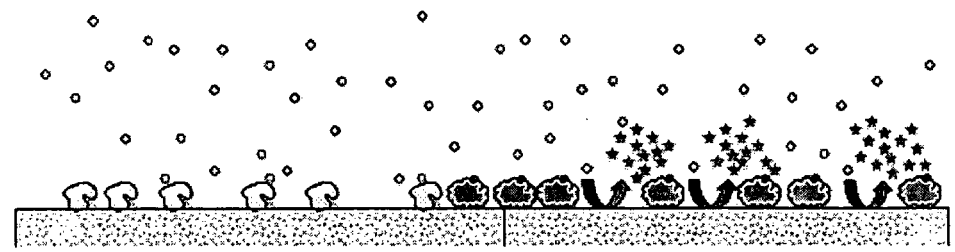

FIG. 10

1. Pattern HRP conjugated to analyte of interest on zone A of a bare gold film
2. Fill zone B with plain BSA
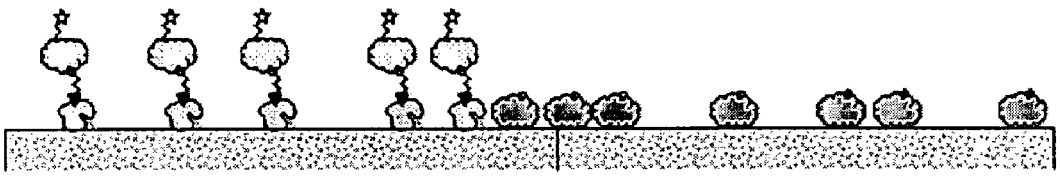
3. Flood with antibody specific to analyte of interest and corresponding competitor analyte
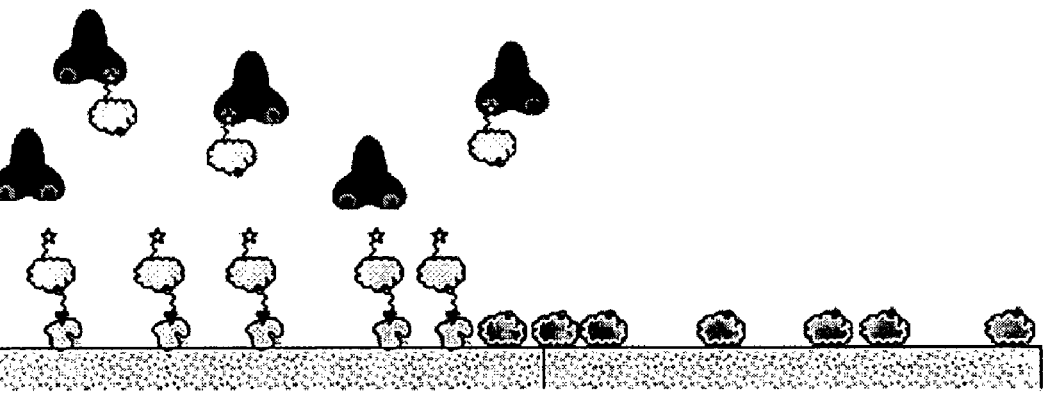
4. Unbound antibody binds to immobilized analyte; Upon binding, antibody inactivates HRP, either through steric or chemical inhibition
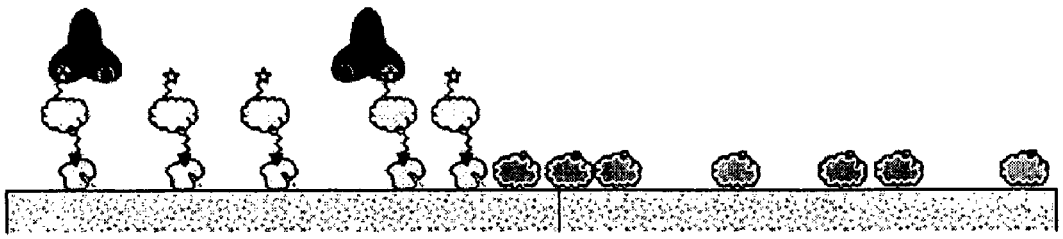
FIG. 11

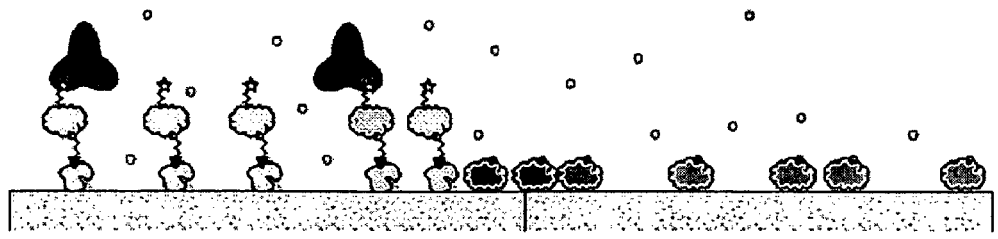
5. Add $H_2O_2$, which rapidly diffuses to HRP layer and oxidizes remaining active molecules.
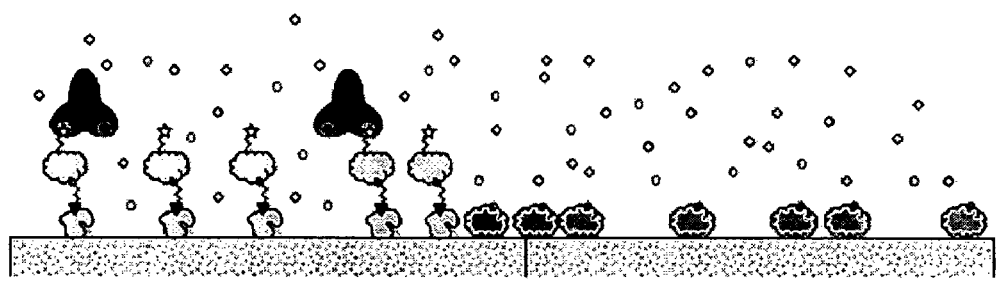
6. Add TMB to whole system
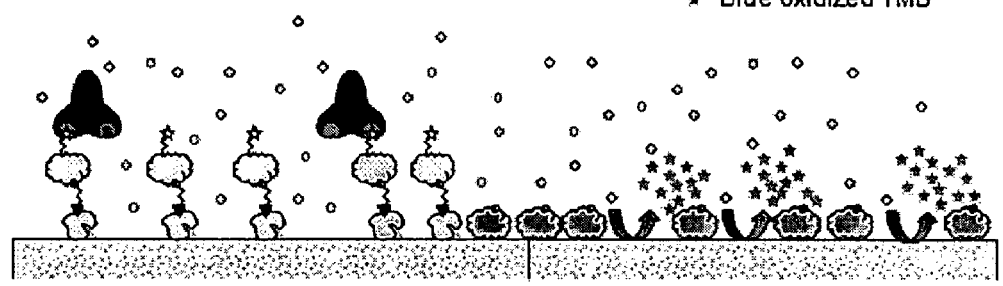
7. Electrons move from zone B to zone A, so TMB converts to blue precipitate primarily at bare gold between BSA in zone B
- Hydrogen peroxide
- TMB
- Blue oxidized TMB
FIG. 11 cont'd 1. Pattern a mix of biotinylated BSA and HRP on zone A of a bare gold film
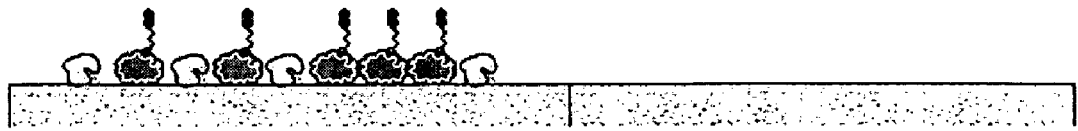
2. Fill zone B with plain BSA
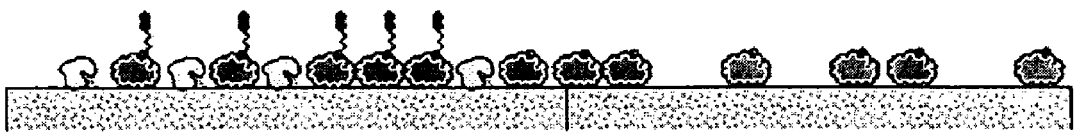
3. Flood with streptavidin, which binds only in zone A
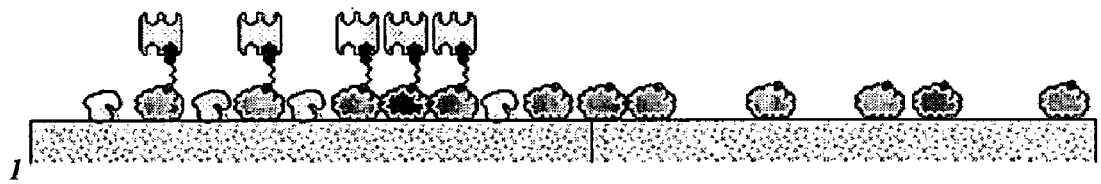
4. Add biotinylated capture antibody
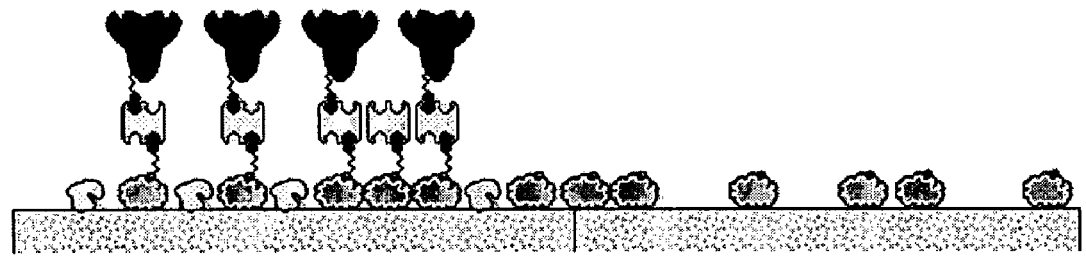
5. Capture bivalent analyte on capture antibodies
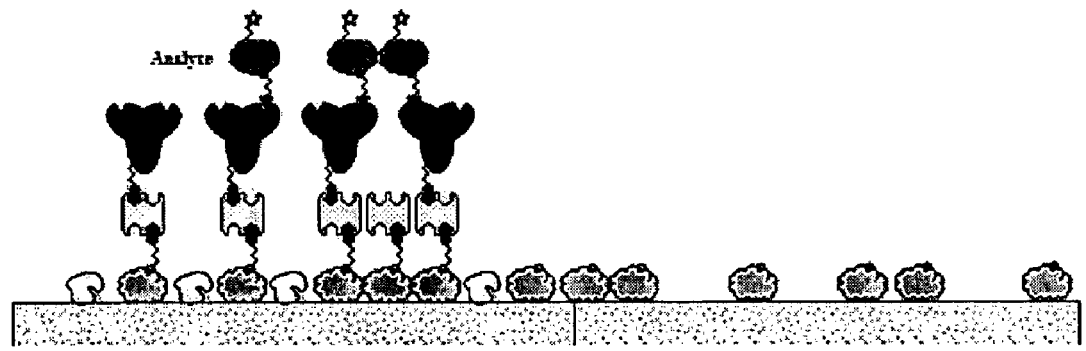
FIG. 12

6. Add secondary antibody labeled with glucose oxidase
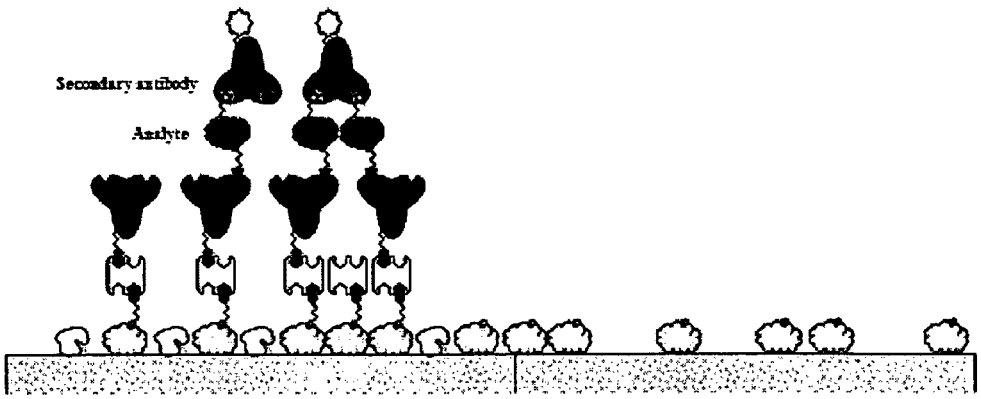
7. Add substrates (glucose and $O_2$) that are converted by glucose oxidase to product and $H_2O_2$. $H_2O_2$ rapidly diffuses to HRP layer, oxidizing HRP
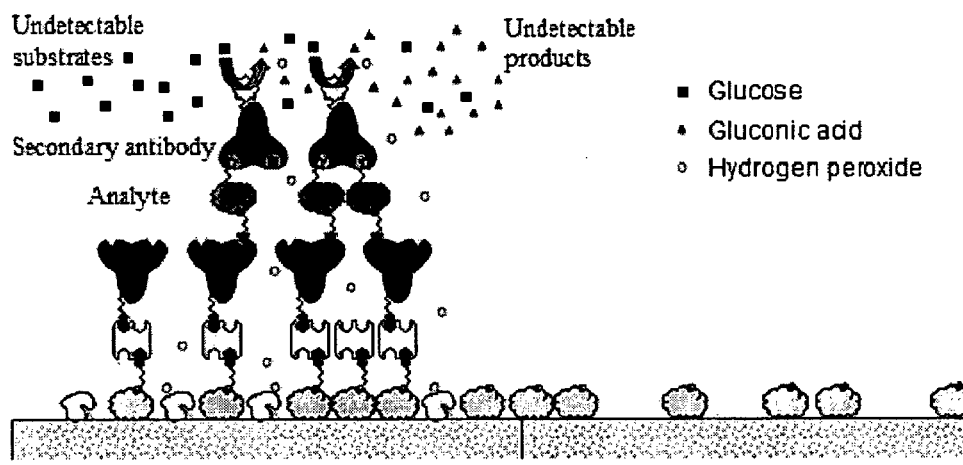
- Glucose
- Gluconic acid
- Hydrogen peroxide
8. Add TMB to whole system
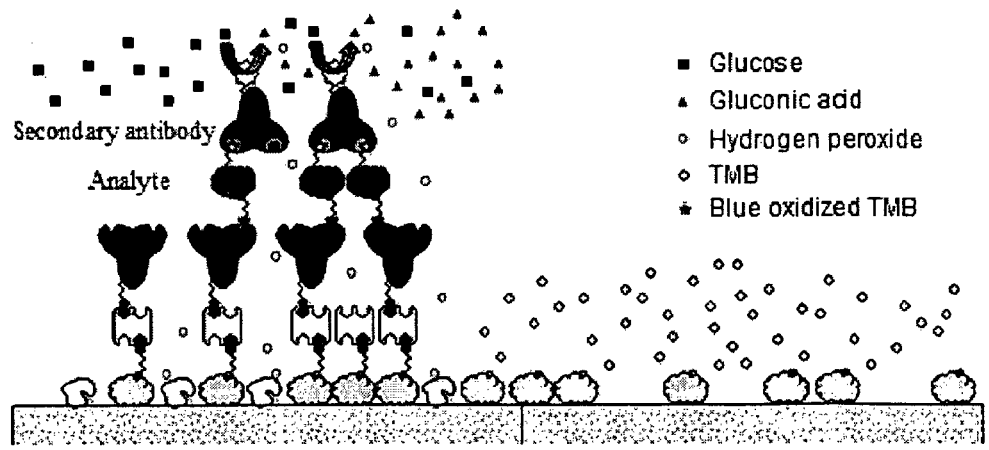
- Glucose
- Gluconic acid
- Hydrogen peroxide
- TMB
- Blue oxidized TMB
FIG. 12 cont'd

CHEMICAL SENSOR ENHANCED BY DIRECT COUPLING OF REDOX ENZYME TO CONDUCTIVE SURFACE

CROSS-REFERENCE TO RELATED APPLICATIONS

This application is a divisional of application Ser. No. 11/364,436, filed Feb. 28 2006, now U.S. Pat. No. 7,364,886 B2, the entire contents of which are incorporated herein by reference.

STATEMENT REGARDING FEDERALLY SPONSORED RESEARCH

The invention disclosed herein was made with Government support under Grant No. 5U01-DE014971-04, awarded by the National Institutes of Health. The government has certain rights in this invention.

TECHNICAL FIELD OF THE INVENTION

This invention relates generally to the manufacture of sensors and methods of using same. The invention amplifies chemical sensor measurements by coupling a redox enzyme to a conductive surface. The invention exploits direct electron transfer to achieve detection remote from the site of the redox enzyme.

BACKGROUND OF THE INVENTION

The well-understood catalytic cycle between horseradish peroxidase (HRP) and its commonly utilized colorimetric substrate, tetramethylbenzidine (TMB), proceeds as follows. First, HRP undergoes a two-electron oxidation of its ferriheme prosthetic group by hydrogen peroxide in solution. The oxidized HRP, known as compound-I, consists of an oxyferryl iron and a porphyrin τ cation radical [Everse, J., et al., *Peroxidases in Chemistry and Biology.* Vol. 1, 1991, Boca Raton: CFC Press. 620]. In the next reaction, the oxidized HRP converts the TMB in bulk solution from its normal reduced state to a colored oxidized form. Specifically, in a first step, a one-electron oxidation of TMB results in the formation of a cation radical intermediate. In a second reaction, the cation radical is further oxidized to form a yellow colored diimine. Two of the intermediate cation radicals may also combine to form a blue charge-transfer complex, which may be readily quantified with spectrophotometry [Josephy, P. D., et at. Journal of Biological Chemistry, 1982. 257(7): p. 3669-3675; Bally, R. W. and T. C. J. Gribnau, J Clin Chem Clin Biochem, 1989. 27(10): p. 791-796]. In the presence of dextran sulfate or other precipitating agents, the normally soluble oxidized form of TMB reacts to form an insoluble dark blue colored precipitate [McKimm-Breschkin, J. L., Journal of Immunological Methods, 1990. 135: p. 277-280]. As a result of the TMB oxidation steps, the enzyme is reduced to its native resting state, and may then be re-oxidized by hydrogen peroxide to restart the cycle. This peroxidase reaction sequence is well known in the literature and has been used for a number of detection schemes [Volpe, G., et al., Analyst, 1998. 123: p. 1303-1307; Alfonta, L., et at., Analytical Chemistry, 2001. 73(21): p. 5287-5295; Loo, R. W., et al., Analytical Biochemistry, 2005. 337(2): p. 338-342].

Direct electron transfer (DET) between an electrode material and redox-active biomolecules was first reported in 1977, and involved the use of cyclic voltammetry measurements of cytochrome-c etectrochemistry [Eddowes, M. J. and H. A. G. Hill, Journal of the Chemical Society—Chemical Communications, 1977. 21: p. 771-772; Yeh, P. and T. Kuwana, Chemistry Letters, 1977. 10: p. 1145-48]. Since these initial reports, efficient direct electron transfer has been documented for a number of redox enzymes, the majority of which contain a metallocenter, namely a heme group [Habermuller, L., et al. Fresenius Journal of Analytical Chemistry, 2000. 366(6-7): p. 560-568; Gorton, L., et al., Analytica Chimica Acta, 1999. 400: p. 91-108]. DET has also been established between HRP and a number of electrode surfaces, including carbon and graphite materials, gold, and platinum [Ruzgas, T., et at., Journal of Electroanalytical Chemistry, 1995, 391: p. 41-49]. HRP is one of the most commonly studied redox enzymes for coupling electron transport directly to conductive surfaces [Ruzgas, T., et al., Journal of Electroanalytical Chemistry, 1995. 391: p. 41-49; Yaropolov, A. I., et al. Bioelectrochemistry and Bioenergetics, 1978. 5(1): p. 18-24; Ferapontova, E., Electroanalysis, 2004. 16: p. 1101-1112]. It is known that this coupling can be used to monitor redox reactions mediated by HRP, such as those involved in biosensor applications, by monitoring current flow to an electrode onto which the HRP is adsorbed [Ghindilis, A. L., et al. Electroanalysis, 1997. 9(9): p. 661-674.].

There remains a need, however, for improved and more flexible methods of amplifying redox reactions used in chemical sensors. The invention disclosed herein addresses these needs and others by providing a means of exploiting electron transfer to remote sites via electrically coupled conductive surfaces.

SUMMARY OF THE INVENTION

The invention provides a method for detecting electrochemical oxidoreduction activity mediated by a redox enzyme at a site remote from the enzyme. In one embodiment, the method comprises immobilizing the redox enzyme on a first region of a conductive surface and contacting a substrate that produces a detectable signal upon oxidation or reduction with at least one additional region of the conductive surface. The additional region is electrically coupled with the first region and the redox enzyme is not present in the additional region. The method further comprises exposing the immobilized redox enzyme to conditions that effect oxidation or reduction of the enzyme, and detecting oxidation or reduction of the substrate at the additional region. Examples of a substrate capable of producing a detectable signal upon oxidation or reduction include a colorimetric or fluorogenic enzyme substrate, such as tetramethylbenzidine (TMB), 4-chloro-1-naphthol (4-CN) and 3,3'-diaminobenzidine (DAB) or dihydroxyphenoxazine (Amplex® Red). In some embodiments, the substrate produces the detectable signal via reaction with an agent and the detectable signal comprises a colorimetric, fluorogenic or precipitating product, such as wherein the substrate is tetramethylbenzidine and the agent is dextran sulfate.

Typically, the redox enzyme comprises horseradish peroxidase, glucose oxidase, alcohol oxidase, lactate oxidase, choline oxidase, cholesterol oxidase, glutmateoxidase or amino acid oxidase. In one example, the conditions that effect oxidation of the redox enzyme comprise contact with hydrogen peroxide. The conductive surface typically comprises a metal film, such as gold, silver, copper, platinum or aluminum film, or carbon or graphite materials.

The electrochemical oxidoreduction activity can be indicative of the presence of an analyte, thereby providing a method for analyte detection. The methods of the invention can be performed using flow or stopped flow conditions. Both the substrate and the analyte can be introduced using flow or stopped flow conditions.

Also provided is an apparatus and system for detecting electrochemical oxidoreduction activity mediated by a redox enzyme at a site remote from the enzyme. The system comprises an apparatus having a conductive surface that has a first region and at least one additional region, and a means for detecting oxidation or reduction of a substrate that produces a detectable signal upon oxidation or reduction at the additional region. In this embodiment, a redox enzyme is immobilized on the first region of the conductive surface, the additional region is electrically coupled with the first region, and the redox enzyme is not present in the additional region.

The invention further provides a method, apparatus and system for detecting a plurality of analytes. The method comprises contacting a solution suspected of containing a plurality of analytes with a plurality of electrically coupled paired regions or sets of electrically coupled regions. Each of the electrically coupled sets of regions is electrically isolated from the other electrically coupled regions and a first region of each of the sets of regions comprises an immobilized redox enzyme that is oxidized or reduced, directly or indirectly, upon contact with an analyte. At least one additional region of each set of regions is in contact with a substrate that produces a detectable signal upon oxidation or reduction. The method further comprises exposing the immobilized redox enzymes to conditions that effect oxidation or reduction of the enzymes, and detecting oxidation or reduction of the substrates at the additional region(s) of each set of regions.

Also provided is a sensor for detecting a plurality of analytes. The sensor comprises a plurality of electrically coupled paired regions or sets of electrically coupled regions, wherein each paired region is electrically isolated from the other paired regions. A first region of each of the paired regions comprises an immobilized redox enzyme that is oxidized or reduced upon contact with an analyte, and at least one additional region of each of the paired regions is electrically coupled with the first region, and the redox enzyme is not present in the additional region. Upon contact with a substrate that produces a detectable signal upon oxidation or reduction, oxidation or reduction of the substrate is detected in the additional region(s).

BRIEF DESCRIPTION OF THE DRAWINGS

FIG. 5. SPR data that indicates precipitate formation at sites remote from the HRP only requires a conductive path between the regions of interest (given HRP redox activity at the initial site and a TMB precipitating substrate solution at the remote site). Specifically, a continuous volume of TMB (or some other component of the bulk substrate solutions between the regions of interest is not required. Sequence of SPR images with TMB in both the upper and lower fluid streams. Five HRP regions were patterned in the upper stream, and PBS was introduced into the center stream. Note the extensive precipitate formation in both TMB-containing streams, including the lower stream, which contained no enzyme. Again, flow is from left to right, and images were captured every 2 seconds. The image numbers were 31, 33, 37, 90, 160, and 200, from left to right, top to bottom.

FIG. 6. Photograph of the final sample described in FIG. 5 above. Good agreement was observed between regions of high SPR intensity and regions of precipitate formation. Note that the SPR instrument used in this work foreshortens the image in the x-dimension.

FIG. 7. Design for a multi-analyte assay. The 3×5 array of rectangular regions (and the two large rectangular regions on either side of the array) were coated with gold. Each region of the array, since it is electrically isolated from the other regions, may be treated as an independent measurement.

FIG. 8. Representative SPR image of the array format before the formation and spreading of the precipitate.

FIG. 9. Representative SPR image of the array format after the formation and spreading of the precipitate. The signal in each of the regions is independent.

FIG. 10. Schematic of a basic embodiment of the invention, where the method is utilized as a sensitive hydrogen peroxide detector.

FIG. 11. Schematic of a competitive immunoassay variation of the present invention.

DETAILED DESCRIPTION OF THE INVENTION

Figure 1:
FIG. 1. Schematic overview of the surface electrochemistry system utilized in the examples described herein, including surface-bound enzymes, a bulk substrate solution, and the resultant precipitation reaction.

The invention is based on the discovery of a novel method of applying the process of direct electron transfer between surface-bound redox molecules and an electrical conductor to the enhancement of chemical detection. The invention relates to direct coupling between a redox enzyme (e.g., horseradish peroxidase, HRP) and a conductive surface as a method of amplifying chemical sensor measurements. The invention is based on a surprising effect of detectable and measurable precipitate formation at sites remote from the redox enzyme that is mediated by electrical coupling through a continuous conductive surface between the sites. This discovery provides for significant amplification of the original signal at sites remote from the original site as well as at the original site. The invention also provides for parallel detection of multiple samples and/or multiple analytes by taking advantage of the ability to electrically isolate different electrochemical reactions.

In general, the method involves two or more conductive regions (or surfaces) that are electrically connected. On one conductive region an electrochemical reaction occurs through any of a number of mechanisms. The electrons gained or lost through this reaction are then transported to or from a second conductive region, where a corresponding electrochemical reaction occurs. This sequence of electron-shuttling reactions occurring at two distinct sites thereby increases the area over which the electrochemical reaction occurs. The electron transport between the aforementioned conductive regions may occur through a number of mechanisms. The specific oxidation and reduction reactions are also wide-ranging, and may include enzymatic redox reactions. This method has utility in a range of electrochemical sensors and also has applicability to a variety of detection platforms, including optical detection methods.

Definitions

All scientific and technical terms used in this application have meanings commonly used in the art unless otherwise specified. As used in this application, the following words or phrases have the meanings specified.

As used herein, "redox enzyme" refers to an enzyme having chemical moiety capable of undergoing a reduction (acceptance of one or more electrons) or oxidation (donation of one or more electrons) between a conductive surface and the enzyme.

As used herein, a "conductive" surface means an electrically conductive surface.

As used herein, "electrically coupled" refers to two or more regions that are electrically coupled with each other.

As used herein, under "flow conditions" refers to a state of continuous liquid solution flow.

As used herein, "stopped flow conditions" refers to a state in which liquid solution flow is halted, such as to allow for measurement or analysis.

As used herein, "a" or "an" means at least one, unless clearly indicated otherwise.

Overview

This novel surface electrochemistry method has been demonstrated using an enzyme precipitation system, in which the surface-bound redox-active molecule is the enzyme HRP, the substrate is TMB, and a precipitating agent having properties similar to dextran sulfate is used. In this demonstration, the conductor was a thin uniform gold film of finite area deposited on an electrical insulator. Note that in this case the gold layer was not electrically coupled to a measuring system.

One of the primary requirements for efficient electron transfer between immobilized redox molecules and an electrode is a short, unobstructed path between the molecule's active site and the electrode surface [Habermuller, L., et al. Fresenius Journal of Analytical Chemistry, 2000. 366(6-7): p. 560-568]. This requirement can be met by direct adsorption of the molecule to the electrode. If this requirement is not met, precipitate formation is localized only to the regions containing HRP. This was demonstrated in recent work involving an enzyme precipitate amplification scheme on a self-assembled monolayer-coated gold surface. In this setup, the redox molecule (HRP) was elevated above the electrode surface, and strict localization of the biocatalyzed precipitate to regions containing HRP was observed [Pyo, H. B., et al., Langmuir, 2005. 21(1): p. 166-171].

Methods

In brief, the present invention involves a method for increasing the area over which an electrochemical reaction occurs following direct electron transfer (DET) between immobilized redox-active molecules and a conductive surface. In a typical embodiment, the redox-active molecule is the enzyme HRP; the electrochemical reactions are a sequence of oxidation and reduction reactions occurring between hydrogen peroxide, HRP, and TMB; the conductive surface is a thin gold film, and the detection method is surface plasmon resonance imaging.

The exemplary method focuses on two conductive regions, denoted zone A and zone B, that are in electrical communication with each other. On zone A, HRP is immobilized in such a way as to allow direct coupling to the gold firm through its heme prosthetic group. To begin the process, the surface-bound HRP molecules are oxidized by the addition of hydrogen peroxide to the buffer surrounding the enzymes. The gold film in zone A, which is in electrical contact with the HRP prosthetic group, then transfers electrons to re-reduce the HRP; the gold firm in zone B (that does not contain HRP) is now biased positive in proportion to the rate of oxidation of the HRP molecules. TMB at the gold film in zone B is then oxidized and thereby converted to an insoluble precipitate at a site remote from the HRP. The novel aspect of this phenomenon is that any conducting region in electrical contact with zone A, even at a remote distance, can be the site of oxidation and precipitation of TMB as long as the HRP at zone A is re-reduced.

The accumulation of the detectable precipitate, which otherwise is limited by the fact that it covers the HRP and prevents influx of chemicals to the immobilized enzyme, is thereby greatly increased via this method. The formation of the insoluble enzyme precipitate on the gold surface may be readily detected qualitatively by eye (the product is dark blue), or quantitatively by optical absorbance, ellipsometry, or SPR-based techniques. We observed rapid signal amplification in electrically coupled remote regions not containing HRP, as well as in the region containing HRP.

The primary application of this phenomenon is the detection of chemicals that either directly or indirectly initiate the oxidation or reduction of the immobilized redox molecule. In the above general description of the invention, the initial reaction may involve a variety of redox-active molecules. The only requirement is that electrons are transferred during the reaction. In addition to direct electron transfer, the electrons may be shuttled to the electrode surface through a variety of mediators [Gorton, L., et al., Analytica Chimica Acta, 1999. 400: p. 91-108]. Likewise, the electrode material may be any conductive material, including noble metals and carbon nanotubes, as long as electrons are readily transferable through the material. The electrical connection between the initial and final reaction regions may be continuous, such as in the case of a single gold coating layer, or it may be a conductive wire that connects the two regions. It is not necessary to employ a precipitating substrate system. The substrate system may produce a colorimetric change, such as in the case of a soluble TMB substrate solution, or a fluorescence change such as in the case of the commercially available Amplex®Red substrate of HRP.

Lastly, the detection and measurement of the electrochemical signal may be accomplished through any technique capable of measuring electrical current and a variety of other techniques that will depend on the specific signal generated by the choice of enzyme-substrate system. For a precipitate-based signal, detection techniques include surface plasmon resonance (SPR)-based techniques (spectroscopy and imaging) and electrochemical quartz crystal microbalance. Fluorescence detection methods would be appropriate for fluorescence-based signals and absorbance measurement systems would be appropriate for signals resulting in a colorimetric change.

The method can also be used to detect multiple analytes. In this embodiment, the sensor comprises a plurality of electrically isolated conductive regions. At each conductive region, a redox enzyme is directly coupled to a portion of the conductive surface. Detection of each analyte is amplified and its signal can be detected independently from the signal from other analytes. Lastly, this method may be applied under static or flow conditions.

Apparatus and System

Figure 13:
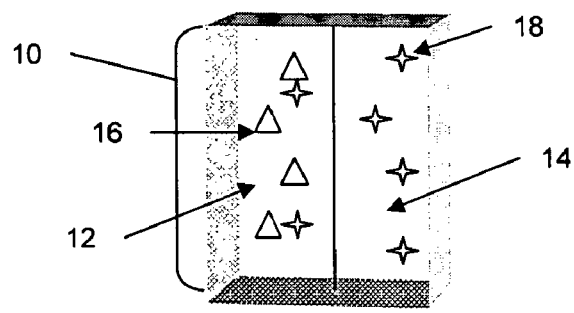
FIG. 13. Schematic illustration of an apparatus of the invention.

A representative apparatus in accordance with the invention is illustrated schematically in FIG. 13. A conductive surface 10 has a first region 12 and at least one additional region 14, wherein the regions are electrically coupled via the conductive surface 10. A redox enzyme 16 is immobilized on the first region 12, but not on the second, or additional region(s) 14. A detectable signal 18 can be produced on both the first region 12 and at least one additional region 14, although a signal need not be generated in the first region. Embodiments adapted for detection of multiple analytes comprise a plurality of sets of electrically coupled regions, wherein each set of electrically coupled regions comprises the elements illustrated in FIG. 13. The plurality of electrically coupled regions are electrically isolated from each other, and the first region 12 of each set of regions can be designed to detect a different analyte.

The apparatus can be part of a system for detecting electrochemical oxidoreduction activity and/or for detection of one or more analytes. The system comprises an apparatus or sensor as described herein and a means for detecting oxidation or reduction of a substrate capable of producing a detectable signal upon oxidation or reduction at the additional region(s). The detectable signal can be detected by any means of signal detection known in the art, such as an optical detection system. Examples of detection systems include but are not limited to: a CCD camera, surface plasmon resonance (SPR)-based techniques (spectroscopy or imaging), electrochemical quartz crystal microbalance, and fluorescence or other optical detection, such as is used in ELISA-based assays. For some embodiments, the detecting means comprises SPR-based techniques (spectroscopy or imaging), electrochemical quartz crystal microbalance, and/or any other technique capable of measuring formation of an insoluble precipitate layer. In addition, a technique capable of measuring electrical current can be used.

EXAMPLES

The following examples are presented to illustrate the present invention and to assist one of ordinary skill in making and using the same. The examples are not intended in any way to otherwise limit the scope of the invention.

Example 1

Lateral Electron Transfer Between Electrically Connected Regions

In this example, we employed an established enzyme precipitation system involving the enzyme horseradish peroxidase (HRP), and its colorimetric substrate, 3,3',5,5'-tetramethylbenzidine (TMB). In brief, the specific enzymatic catalytic cycle is as follows. HRP is first oxidized by hydrogen peroxide, the oxidized HRP then, in turn, oxidizes a molecule of TMB into an insoluble blue form that, upon reaction with a precipitating agent, results in precipitate formation; the reduced HRP is subsequently re-oxidized by hydrogen peroxide, and the cycle can begin again [Everse, J., et al., *Peroxidases in Chemistry and Biology*, Vol. 1. 1991, Boca Raton: CFC Press. 620]. The general experimental protocol in the initial demonstration involved HRP directly adsorbed to a gold surface, such that electrons may be transferred between the conductive surface and the enzyme's heme prosthetic group [Ruzgas, T., et al., Journal of Electroanalytical Chemistry, 1995. 391: p. 41-49; Yaropolov, A. I., et al. Bioelectrochemistry and Bioenergetics, 1978. 5(1) p. 18-24; Ferapontova, E., Electroanalysis, 2004. 16: p. 1101-1112]. Upon addition of TMB, electrons are transferred between electrically connected gold regions, and the substrate is rapidly converted to an insoluble precipitate at sites remote from the surface-immobilized HRP molecules. The precipitate formation is detected by surface plasmon resonance imaging (SPRI) or optical absorption of light reflected by the gold surface. This phenomenon greatly increases the area over which the electrochemical reaction occurs and thus amplifies the original signal. The primary application of this method is the detection of chemicals that either directly or indirectly affect the oxidation or reduction of redox molecules immobilized on a conductive surface.

These experiments show that the electrochemical precipitate spreading process is rapid and significant. FIG. 1 schematically depicts the system used to investigate this method. The enzyme used in this investigation was horseradish peroxidase (Sigma-Aldrich, St. Louis, Mo., USA) in phosphate buffered saline (PBS) and the substrate solution was 3,3',5,5'-tetramethylbenzidine (United States Biological, Swampscott, Mass., USA) in an acetate buffer containing hydrogen peroxide and precipitating agents. The first step of the demonstration involved patterning the enzyme solution directly onto a gold-coated microscope slide using a piezoelectric inkjet printing system (MicroFab Technologies, Plano, Tex., USA). Thus, as required by the electrochemistry process, a redox-active molecule was placed in close proximity to a conductive surface.

For most experiments, a microfluidic flow cell was then assembled from laminate sheets of Mylar® (Fralock, Santa Clara, Calif., USA) and adhesive, and the pre-patterned gold-coated microscope slide was used as the bottom layer of the flow cell. The assembled microfluidic flow cell was then fitted into a manifold on a custom-built SPR microscope [Fu, E., et al., Review of Scientific Instruments, 2004. 75(7): p. 2300-2304; Fu, E., et al. Review of Scientific Instruments, 2003. 74(6): p. 3182-3184] and rinsed with PBS to remove any free and/or loosely adsorbed HRP molecules. A controlled, laminar flow rinse was performed to ensure that the excess HRP would only be deposited downstream of the patterned regions.

After establishing baseline SPR images with PBS as the bulk fluid, the TMB solution was pumped through the microfluidic flow cell at a rate of 1 μl/s through the use of syringe pumps (Kloehn, Las Vegas, Nev. USA). The sensor surface was monitored via the SPR microscope throughout the course of the electrochemical and enzyme precipitation reactions. Finally, the TMB solution was rinsed from the sensing cell using PBS and the signal amplification and electrochemical spreading due to the precipitate formation was examined both qualitatively and quantitatively using SPR imaging.

Figure 2:
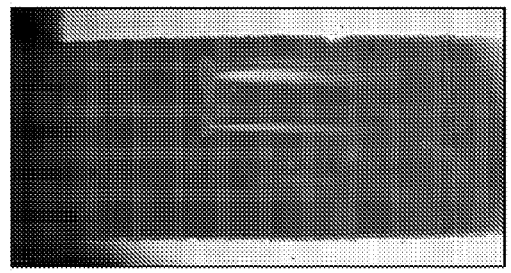
FIG. 2. Surface plasmon resonance (SPR) image of the pump-controlled HRP rinse-out procedure with PBS, with flow from left-to-right. The arrow corresponds to the general lateral position of the patterned enzyme regions. Note that excess HRP in the original patterned regions of the gold surface is deposited downstream of the original patterns after rinsing with PBS, i.e., there is no HRP on the gold surface upstream of or lateral to the original patterns.

SPR images of the HRP rinse-out procedure, such as that in FIG. 2, where flow was in the left-to-right configuration, suggested that transport of any excess enzyme in the patterned regions was restricted to the downstream regions of the laminar flow rinse (right side of the patterns in the image).

Figure 3:
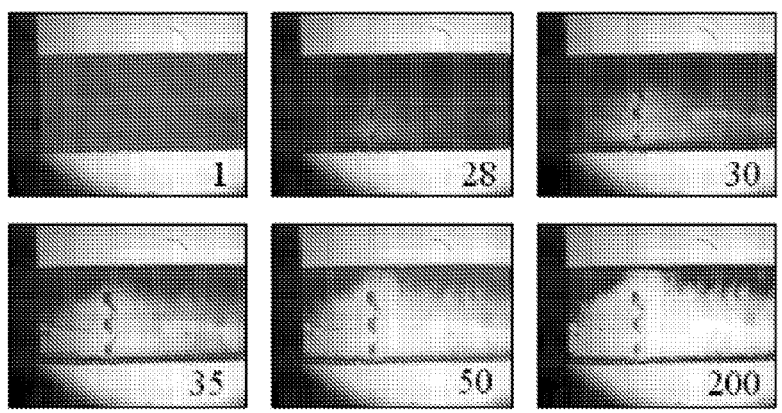
FIG. 3. SPR images throughout the addition of TMB and a subsequent rinse with PBS. Flow is from left-to-right in all images. The numbers correspond to image number, where images were captured every 2 seconds. Note that the TMB precipitate rapidly appears in regions without HRP, e.g., upstream of the location of the original HRP patterns.

The time sequence following the introduction of TMB to the SPR sensing cell is illustrated in the SPR images in FIG. 3. In all images, flow was in the left-to-right orientation. The numbers in the lower-right corners correspond to the image number, which were captured every two seconds. The three dark rectangular regions correspond to the patterned enzyme areas. The final image depicts the gold surface following extensive rinsing with PBS. Note that the precipitate remained after rinsing and was neither restricted to the patterned regions nor discrete regions to the right of the patterned patch where excess HRP may have adsorbed during the initial rinse. The precipitate either formed at or became localized to regions that contained no enzyme (both upstream of and lateral to the original enzyme patches), suggesting extensive electron transfer throughout the gold surface.

Figure 4:
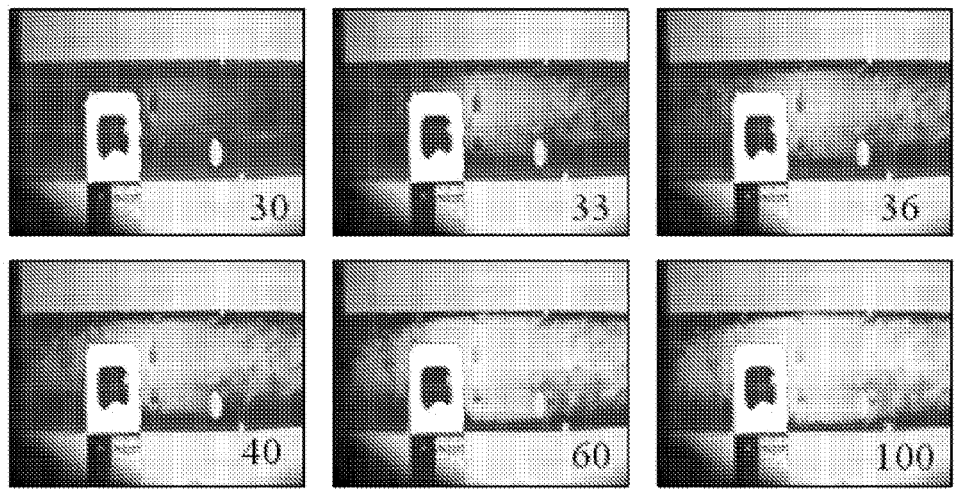
FIG. 4. SPR data that indicates precipitate formation at sites remote from the HRP requires a conductive path between the regions of interest. The precipitate forms in the bare gold region upstream of and electrically couple to the patterned HRP. However, the precipitate does not form in the isolated bare gold region upstream of the patterned HRP. Again, flow is from left to right, and images were captured every 2 seconds.
Figure 12:
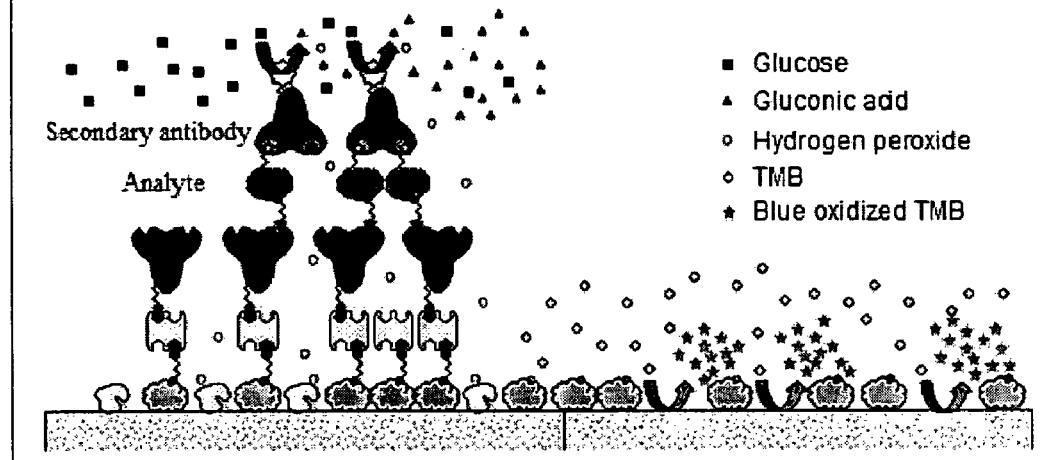
FIG. 12. Integrated scheme of the present invention, involving a second enzyme that generates hydrogen peroxide in proportion to the amount of bivalent sample antigen present.

This general experimental protocol was then modified in a subsequent experiment, where a specially designed Mylar® mask was applied to the microscope slides during the gold deposition process, such that a region of the slide contained an electrically isolated "island" of gold. This conductive region, of dimensions 2 mm by 2 mm, was surrounded on all sides by a 1 mm-wide region of insulating glass. Small regions of 0.1 mg/ml HRP were then patterned with the piezoelectric microdispenser downstream of the isolated gold region. A single-channel microfluidic flow cell was then affixed to the protein patterned slide and the TMB solution was pumped through the microchannel as before, with flow in the left-to-right orientation. As in previous experiments, the precipitate was observed to spread rapidly to regions not containing any enzyme. However, the gold region electrically isolated by the region of glass remained free of the precipitate. This result is depicted in the time sequence of images in FIG. 4, and demonstrates the requirement of an electrical connection between the HRP region and the region not containing HRP, in order to obtain precipitation formation in the latter.

The electrochemical mechanism involved in this invention disclosure was further exemplified in an experiment involving three microfluidic streams flowing in parallel in a single microchannel. This three-inlet microfluidic configuration allowed for the physical separation of two TMB solution streams, one in contact with immobilized enzyme patterned directly on the gold surface and one in contact with a bare gold region at the opposite wall of the microchannel. Note that this second stream was not in contact with any enzyme molecules. The center stream contained only buffer, and the widths of the various streams were varied to control the electron transfer distance.

After patterning the enzyme in discrete rectangular regions, the substrates were rinsed thoroughly with PBS under microfluidic flow conditions. As illustrated in the sequence of SPR images in FIG. 5, TMB was introduced into both the upper (enzyme-containing region) and lower (no enzyme in the region) fluid streams, with the center buffer stream occupying a relatively small width (~15%) of the entire microchannel. With TMB already in the lower stream, no precipitate formation was observed until TMB was also present in the upper enzyme-containing stream. As indicated in the sequence of images, rapid and significant formation and spreading of the precipitate was then observed in both the upper and lower portions of the channel. This result indicates that the only requirement for precipitate formation at a site remote from the HRP region, given HRP activity at the initial site and a TMB precipitating substrate solution at the remote site, is an electrical connection between the regions. Specifically, a continuous volume of TMB (or some other component of the bulk substrate solution) between the regions of interest is not required.

This result was verified visually, as presented in FIG. 6, as the blue precipitate was present along the length of the channel in stripes along the upper and lower walls of the channel, i.e. in the same pattern observed in the SPR images.

To explore the utility of the present invention in future quantitative assays, including those involving the detection of multiple analytes, a preliminary experiment was performed that investigated the effect of a range of enzyme concentrations on the extent of the electrochemistry reaction. It was expected that different enzyme concentrations (and/or peroxide concentrations) would generate different rates of precipitate formation in the regions surrounding the enzyme patterns (i.e. regions not containing enzyme). To begin, microscope slides were selectively patterned with a thin gold layer, generating fifteen isolated 1 mm×1 mm squares of conductive gold. The Mylar® mask design used during the gold deposition process is shown in FIG. 7, where regions outlined in blue represent regions to be covered with gold. HRP was then patterned onto each of the fifteen gold-coated square regions as described above. The slides received different volumes of 0.01 mg/ml HRP, effectively functionalizing the gold surfaces with different enzyme concentrations. Patterning with both a low droplet density and a low protein concentration ensured sub-monolayer protein coverage. A TMB solution was then added to each slide, initiating the electrochemical process, and the reaction was monitored via SPR microscopy.

FIGS. 8 and 9 depict representative SPR images of a patterned gold slide with localized enzyme regions before and after the formation and spreading of the precipitate, respectively. In FIG. 9, the enzyme regions appear as the dark rectangular regions within the fifteen rectangles; the higher intensity regions surrounding the patterned enzyme zones represent the precipitate, and the surrounding brighter regions are the bare glass substrate. No visable precipitate formation was observed on the glass regions. Potential methods of quantification of the signal include the rate of precipitate formation or an end-point precipitate signal measurement. This result also suggests the potential for rapid detection and amplification of multiple analytes in parallel.

Example 2

Chemical/Biochemical Detection Schemes Utilizing this Novel Detection Method

This method is generally applicable to any technique involving the detection of chemicals that either directly or indirectly produce the oxidation or reduction of an immobilized redox molecule. This includes a range of biosensor applications, including those detailed in the following schemes. Note that while the discussion of these schemes includes specific molecules, reactions, and conductive surfaces to aid in comprehension, the actual schemes should not be limited to these specific examples.

Scheme 1. The schematic in FIG. 10 depicts a basic representation of the present invention. In this scheme, HRP is immobilized on a gold substrate and the addition of hydrogen peroxide followed by TMB (plus precipitating agents) causes the surface electrochemistry and precipitation reactions to occur at sites remote from the HRP, as described in detail in previous sections. BSA is added in the second step in order to block the surface against non-specific binding. In this context, the present invention may be used as a sensitive hydrogen peroxide sensor.

Scheme 2. A straightforward modification of this first scheme adds extensive utility to the invention. This second class of schemes involves the indirect detection of a range of analytes through the concomitant generation and detection of peroxide. For example, a large number of enzyme oxidases exist that, by definition, react with molecular oxygen to catalyze the oxidation of a substrate. A by-product of this reaction is often hydrogen peroxide, which may be detected as in Scheme 1 above.

As a specific example of this scheme, imagine that glucose oxidase is either immobilized or in bulk solution upstream of a pre-patterned HRP region on a conductive surface. With the addition of the appropriate substrates, in this case, glucose and molecular oxygen, the glucose oxidase enzyme will produce hydrogen peroxide in proportion to the amount of glucose present. With the exception that hydrogen peroxide will now be generated internally as part of an additional reaction, steps 3-5 of Scheme 1 will then be followed directly, resulting in a sensitive glucose detector. Alternatively, the glucose oxidase molecules may be substituted with any of the following examples of oxidizing enzymes to be a sensitive detector for a range of analytes: alcohol oxidase, lactate oxidase, choline oxidase, cholesterol oxidase, glutamate oxidase, and amino acid oxidase [Ruzgas, T., et al., Analytica Chimica Acta, 1996. 330: p. 123-138].

Scheme 3. Another possible scheme, which integrates a competitive immunoassay with the novel surface electrochemistry system, is depicted in FIG. 11. With HRP conjugated to an analyte of interest and immobilized on the conductive surface, a solution containing the corresponding antibody and competitor analyte molecules is added to the system. Binding of the available antibody molecules (singly or non-bound) to the surface-immobilized analytes then inactivates those HRP molecules, either through stern or chemical inhibition. Alternatively, the antibody may be linked to a specific inhibitor of the enzymatic reaction. Either way, the extent of precipitate formation and spreading is dependent upon the amount of analyte captured.

Scheme 4. The final scheme of the present invention, which is depicted in FIG. 11, is a more complex and integrated version of Scheme 2 outlined above. The underlying principle remains the same, whereby the formation of hydrogen peroxide is proportional to the presence of another analyte and indirectly generates the electrochemical signal highlighted in this invention disclosure. Specifically, the hydrogen peroxide, a key initiating component of the TMB precipitation reaction, is generated by an enzyme conjugated to a secondary antibody specific to the desired analyte of interest. This highly integrated scheme therefore further broadens the utility of the invention, such that any bivalent analyte may be linked to the formation of hydrogen peroxide and the initiation of this novel electrochemistry reaction. Note that, in the example below, glucose oxidase is used as a model enzyme label for the secondary antibody, but any enzyme that produces hydrogen peroxide (or another molecule capable of oxidizing HRP or another redox enzyme) as a product of a chemical reaction could be utilized.

Throughout this application various publications are referenced. The disclosures of these publications in their entireties are hereby incorporated by reference into this application in order to describe more fully the state of the art to which this invention pertains.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A sensor for detecting a plurality of analytes comprising a plurality of sets of electrically coupled regions, wherein each set of regions is electrically isolated from the other sets of regions and wherein each set of regions comprises:
   (a) a continuous conductive surface having a first region and at least one additional region, wherein a redox enzyme is immobilized on the first region of the conductive surface, wherein the additional region is electrically coupled via the continuous conductive surface with the first region, and the redox enzyme is not present in the additional region; and
   (b) means for detecting oxidation or reduction of a substrate located at the additional region, wherein the substrate is capable of producing a detectable signal upon oxidation or reduction at the additional region.

2. The sensor of claim 1, wherein the means for detecting oxidation or reduction comprises fluorescence or absorbance.

3. The sensor of claim 1, wherein the means for detecting oxidation or reduction comprises surface plasmon resonance.

4. A method for detecting a plurality of analytes comprising:
   (a) contacting a solution suspected of containing a plurality of analytes with the sensor of claim 1,
   (b) contacting at least one additional region of each set of regions with a substrate that produces a detectable signal upon oxidation or reduction;
   (c) exposing the immobilized redox enzymes to conditions that effect oxidation or reduction of the enzymes; and
   (d) detecting oxidation or reduction of the substrates at the additional region of each set of regions.

5. The method of claim 4, wherein the contacting of steps (a) and (b) comprises introducing the solution under flow or stopped flow conditions.

6. The method of claim 4, wherein the contacting of steps (a) and (b) is concurrent.

7. The method of claim 4, wherein the substrate that produces a detectable signal upon oxidation or reduction comprises a colorimetric or fluorogenic enzyme substrate.

8. The method of claim 4, wherein the substrate produces the detectable signal via reaction with an agent and the detectable signal comprises a colorimetric, fluorogenic or precipitating product.

9. The method of claim 4, wherein the redox enzyme comprises horseradish peroxidase, glucose oxidase, alcohol oxidase, lactate oxidase, choline oxidase, cholesterol oxidase, glutamate oxidase or amino acid oxidase.

10. The method of claim 4, wherein the conditions that effect oxidation of the redox enzyme comprise contact with hydrogen peroxide.

11. The method of claim 4, wherein the substrate comprises tetramethylbenzidine (TMB), 4-chloro-1-naphthol (4-CN) and 3,3'-diaminobenzidine (DAB) or dihydroxyphenoxazine (AMPLEX® Red).

12. The method of claim 11, wherein the substrate is tetramethylbenzidine and the agent is dextran sulfate.

13. The method of claim 4, wherein the conductive surface comprises a metal film.

14. The method of claim 13, wherein the metal comprises gold, silver, copper, platinum or aluminum.

15. The method of claim 4, wherein the electrochemical oxidoreduction activity is indicative of the presence of an analyte.

* * * * *